United States Patent [19]

Monti et al.

[11] Patent Number: 5,614,536

[45] Date of Patent: Mar. 25, 1997

[54] SUBSTITUTED N-AMINOALKYLMETHANE SULFANILIDE AS ANTISPASMODICA

[75] Inventors: Carlos E. A. Monti; Gustavo E. Aldomá, both of Buenos Aires, Argentina

[73] Assignee: Roemmers S.A.I.C.F., Argentina

[21] Appl. No.: 178,512

[22] Filed: Jan. 7, 1994

[30] Foreign Application Priority Data

Jan. 13, 1993 [DE] Germany ............ 43 00 696.5

[51] Int. Cl.$^6$ ............ A61K 31/445; A61K 31/40; A61K 31/495; A61K 31/535

[52] U.S. Cl. ............ 514/331; 514/238.2; 514/255; 514/428; 544/160; 544/398; 546/232; 548/569; 564/89

[58] Field of Search ............ 544/160, 398; 546/232; 548/569; 564/89; 514/238.2, 255, 331, 428

[56] References Cited

U.S. PATENT DOCUMENTS

| | | | |
|---|---|---|---|
| 3,531,522 | 9/1970 | Nelson | 546/232 |
| 3,840,597 | 10/1974 | Moore | 564/99 |
| 3,876,651 | 4/1975 | Subirana | 546/347 |
| 4,055,650 | 10/1977 | Dlarge | 514/347 |

FOREIGN PATENT DOCUMENTS 0330065  2/1989  European Pat. Off. ...... C07D 295/12

OTHER PUBLICATIONS

Morrison & Boyd, Organic Chemistry, 2d. ed., Allyn & Bacon, Boston, pp. 334–335 (1966).

Chemical Abstracts, 107: 70814v (2).

*Primary Examiner*—Ceila Chang
*Attorney, Agent, or Firm*—Webb Ziesenheim Bruening Logsdon Orkin & Hanson, P.C.

[57] ABSTRACT

Substituted N-aminoalkylmethane sulfanilide of formula (I), their solutions and pharmaceutically acceptable addition salts, their pharmaceutical compositions and their therapeutic use. In formula (I) Y represents hydrogen, cyano, nitro, amino, acetamide or halogen; n is an integer between 2 and 4, $R^1$ and $R^2$ equal or different are alkyl-(C1-C4) or they are connected together and with the N-atom thereby forming a 1-pyrrolidinyl, 1-piperidinyl, 1-piperazinyl, 4-methyl-1-piperazinyl, 4-ethylpiperazinyl, 4-propylpiperazinyl, 1-homopiperidinyl or 4-morpholine residue. The products of formula (I) are used as antispasmodic agents.

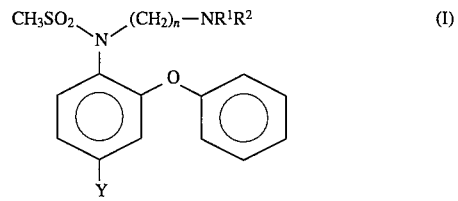

4 Claims, No Drawings

SUBSTITUTED N-AMINOALKYLMETHANE SULFANILIDE AS ANTISPASMODICA

The present invention concerns novel, substituted N-aminoalkylmethane sulfanilides, their solutions and pharmaceutically acceptable addition salts, their pharmaceutical compositions and the therapeutical use in particular as antispasmodics.

State of the art

Various pharmaceutical principles of action are known which are employed in therapeutics for the production of antispasmodics, e.g. medicaments which alleviate spasms of smooth muscles. These medicaments or active agents are separated into two groups: Anticholinergics (or neurotropes) and musculotropes.

The known antispasmodic active agents of the anticholinergic type acting against acetylcholine in the muscarine receptors comprise natural alkaloides (atropine, escopolamine, hyoscyamine), natural alkaloide derivatives (butylescopolamine bromide, octatropine-methylbromide), synthetic tertiary amines (amykeline, trimebutine) and synthetic quaternary ammonium salts (clydinbromide, pinaverium, propanteline and valetamate bromide). This group of antispasmodic active agents exhibits clinical difficulties insofar as undesired side effects are observed such as mydriases, blurring of vision, constipation, inhibition of salivation and tachycardia.

The known antispasmodic agents of the musculotrope type which act upon the muscle by way of an unknown mechanism contain mebeverine, papaverine and pramiverine. The clinical usefulness of this group of pharmaceutical active compounds was questioned and its use is generally reserved for cases where anticholinergica are contra-indicated. Rociverine was the first antispasmodic agent which was mentioned in conjunction with an equilibrium between the anticholinergic and the musculotropic activity.

Thus the problem to find antispasmodic products having little undesired side effects is not solved completely in the therapy of human beings and animals.

The present invention solves this problem by providing a group of chemical by novel products of the substituted N-aminoalkylmethane sulfanilide type which should in particular be used in the therapy as antispasmodic agent. There is no structural similarity between the products according to the present invention and antispasmodic agents known in the prior art. The seemingly closest products from the chemical point of view are described in U.S. Pat. No. 3,840,597. However, none of these products comprises an N-aminoalkyl group in its structure. Moreover, they are used as anti-inflammatory agents only without the possibility of their use as spasmolytic agent having been described anywhere.

Description

The subject matter of the present invention is to provide a substituted N-aminoalkylmethane sulfanilide according to formula (I), a solution or a salt the administration of which is pharmaceutically acceptable,

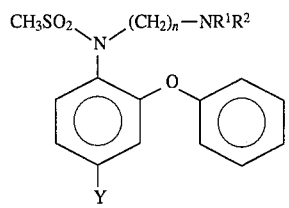

wherein
Y represents hydrogen, cyano, nitro, amino, acetamide or halogen;
n is an integer between 2 and 4;
$R^1$ and $R^2$ are equal or different and represent (C1-C4)-alkyl or are connected via the N-atom, thereby forming preferably a 1-pyrrolidinyl, 1-piperidinyl, 1-piperazinyl, 4-methyl-1-piperazinyl, 4-ethylpiperazinyl, 4-propylpiperazinyl, 1-homopiperidinyl (1-aza-cycloheptanyl) or 4-morpholin residue.

According to the present invention the products of general formula (I) are preferably employed, wherein n equals 2 or 3, including such products in which Y represents nitro, cyano or halogen. Particularly preferred are products in which $R^1$ and $R^2$, that are equal or different are methyl ethyl or isopropyl or are connected with each other and with the N-atom, thereby forming a 1-pyrrolidinyl, 1-piperidinyl, 1-homopiperidinyl (1-aza-cycloheptanyl) or 4-morpholine residue, 1-piperidinyl being the most preferred residue.

The most preferred products according to the present invention are those which correspond to general formula (I) and are indicated explicitly in the examples (table 1). These products will be described here for the first time.

Products (I) according to the present invention are useful in the therapy, in particular as antispasmodic agents. Therefore, the use of these products for the preparation of antispasmolytic medicaments is also the subject matter of the present invention.

Products (I) according to the present invention are administered to human beings or animals by medicament compositions containing therapeutically effective amounts of the product and appropriate amounts of pharmaceutically acceptable excipients. Subject matter of the present invention is also a process for the preparation of medicament composition including the mixing of therapeutically effective amounts of products (I) with the desired amounts of suitable excipients.

Another subject matter of the present invention is to provide a process for the preparation of a product (I) comprising the following steps:
A) when Y is hydrogen or nitro, sulfanilide (II) or (III) must react, respectively, with T—$(CH_2)_n$—$NR^1R^2$, wherein T represents a leaving group that can be displaced by the N of sulfanilides (II) or (III);

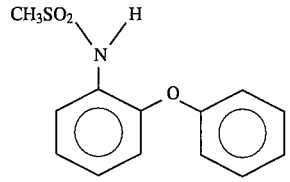

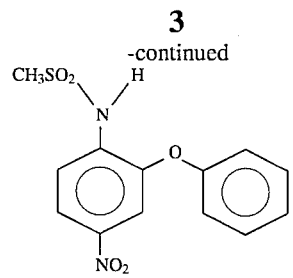

(III)

B) when Y represents amino the corresponding product (I) is reduced in which Y represents nitro by way of catalytic hydrogenation;

C) when Y represents acetamide, the corresponding product (I) in which Y represents amino, reacts with a T-COCH$_3$-reagent in which T is a leaving group;

D) when Y represents cyano or halogen, the corresponding product (I) in which Y represents amino, is subjected to a Sandmeyer reaction (HNO$_2$ and copper cyanide or copper halogenide); and optionally the acid necessary for the formation of the desired addition salt is added.

In method A the leaving group T preferably comprises chlorine, bromine, methylsulphonyloxi or 4-methylphenyl-sulphonyloxi. In the best mode the reaction is performed in the presence of an equimolar or excess amount of an inorganic base, preferably of an alkaline or alkaline earth metal, such as sodium carbonate, potassium carbonate, barium carbonate, potassium bicarbonate or sodium hydroxide; or in the presence of a tertiary organic base such as triethylamine or pyridine. Suitable as solvents are preferably lower alcohols such as ethanol, isopropanol (to be preferred) or secondary butylalcohol; a ketone such as acetone (to be preferred), methylethylketone, methylisobutylketone or cyclohexanol; or a dipolar solvent such as DMF, DMSO or acetonitrile. The temperatures are preferably between ambient temperature and 150° C. and the reaction times preferably are between 1 h and several days.

In method B, the catalytic hydrogenation is performed preferably at pressures of between 1 and 5 atm; especially preferred is a pressure of approximately 2 atm; the catalyst may be palladium (to be preferred), platin or platin oxide. The reaction period is preferably between 30 min. and several hours and the reaction is carried out at temperatures between ambient temperature and 60° C. The solvents are preferably lower alcohols, such as ethanol, water or acetic acid.

In method C the T of the reagent T-CHCH$_3$ preferably is chlorine or OCOCH$_3$. The reaction is carried out in the presence of a base which, if liquid, may act as solvent. Other preferred solvents are aromatic hydrocarbons such as toluene or xylene, ether such as dioxane, halogenated hydrocarbons such as dichloromethane or chloroform. The reaction is preferably carried out at temperatures of between −20° and 150° C. for 1 to 24 h.

In method D the typical conditions according to the Sandmeyer reaction are fulfilled.

Products (I) may be isolated or purified as free bases or preferably as pharmaceutically acceptable addition salts of organic or inorganic acids. The salts of hydrochloric acid or oxalic acid are preferred.

The invention is illustrated in the following examples: The experimental results of the antispasmodic action show that the employed products (I) are therapeutical useful.

EXAMPLES

Examples for synthesis method A: Preparation of the hydrochloride of N-2-(dimethylaminol-ethyl-2-phenoxy-4-nitromethane sulfanilide (1)

A mixture of 3.08 g 2-phenoxy-4-nitromethane sulfanilide (described in U.S. Pat. No. 3,840,597) was reacted with 4.24 g sodium carbonate in 80 ml acetone and refluxed over 6 hours. Thereafter 2.88 g 2-chloroethyldimethylamine-hydrochloride were added and a reflux was maintained while vigorously stirring for 30 h. Thereafter it was filtered and the solvent was evaporated. The residue was dissolved in dichlormethane and washed several times with an NaCl-saturated aqueous solution. The solvent of the organic phase was evaporated. The residue was dissolved in isopropanol. HCl was added to the obtained solution until a pH-value of approximately 2.0 was reached, whereby a yield of 89% of the title compound is obtained. After recristallization in isopropanol, the melting point was determined to be 180°–30° C.

Products 2–8 and 24 of table 1 were obtained in a similar way, i.e. starting from 2-phenoxy-4-nitromethane sulfanilide and the corresponding chloroalkylamine-hydrochlorides with the formula Cl—(CH$_2$)$_n$—NR$^1$R$^2$. Said table shows the yields obtained and the melting points determined.

Preparation of N-[2-(4,morpholinyl)ethyl]-2-phenoxymethane sulfanilide-hydrochloride (13)

A mixture of 1.32 g 2-phenoxymethane sulfanilide (described in US 3,840,597) and 2.12 g sodium carbonate in acetone was refluxed for about 6 h. 1.86 g N-(2-chloroethyl)-morpholin-hydrochloride was added and refluxed for about 25 hours. Thereafter the reaction mixture was cooled to ambient temperature, filtered and the solvent was evaporated. The residue was dissolved in dichloromethane, washed several times with water and the solvent of the organic phase was evaporated. The residue was dissolved in absolute ethanol and acidified with HCl (10% in ethanol), a yield of 91% of the title product (13) having been obtained. After recristallization the melting point was determined to be 173°–4° C.

Products 14–18 in table 1 were obtained in an analogous way, i.e. starting from 2-phenoxy-methanesulfanilide and the corresponding chloroalkylamine-hydrochlorides of the formula Cl—(CH$_2$)$_n$—NR$^1$R$^2$. Said table shows the yields obtained and the melting points determined.

TABLE 1

Prepared products 1 - 21: Hydrochlorides acc. to formula (I)

| No. | n. | Y | NR$^1$R$^2$ | Yield (%) | melting point (°C) |
|---|---|---|---|---|---|
| 1 | 2 | NO$_2$ | N(CH$_3$)$_2$ | 89 | 128–30 |
| 2 | 2 | NO$_2$ | N(CH$_2$CH$_3$)$_2$ | 83 | 155–7 |
| 3 | 2 | NO$_2$ | 1-piperidinyl | 88 | 213–5 |
| 4 | 2 | NO$_2$ | 1-pyrrolidinyl | 81 | 157–9 |
| 5 | 2 | NO$_2$ | N(CH(CH$_3$)$_2$)$_2$ | 68 | 195–7 |
| 6 | 2 | NO$_2$ | 4-morpholinyl | 89 | 245–7 |
| 7 | 2 | NO$_2$ | 4-methyl-1-piperazinyl | 39 | 246–8 |
| 8 | 3 | NO$_2$ | 1-piperidinyl | 75 | 204–8 |
| 9 | 2 | NH$_2$ | 1-piperidinyl | 90 | 220–2 |
| 10 | 2 | NH$_2$ | N(CH$_2$CH$_3$)$_2$ | 80 | 160–2 |
| 11 | 2 | NHCOMe | N(CH$_2$CH$_3$)$_2$ | 87 | 183–5 |
| 12 | 2 | NHCOMe | 1-piperidinyl | 98 | 158–9 |
| 13 | 2 | H | 4-morpholinyl | 91 | 173–4 |
| 14 | 2 | H | N(CH$_3$)$_2$ | 67 | 196–8 |
| 15 | 2 | H | N(CH$_2$CH$_3$)$_2$ | 78 | 180–2 |
| 16 | 2 | H | 1-piperidinyl | 50 | 152–4 |
| 17 | 2 | H | N CH(CH$_3$)$_2$)$_2$ | 47 | 165–7 |
| 18 | 2 | H | 1-pyrrolidinyl | 51 | 165–7 |
| 19 | 2 | CN | 1-piperidinyl (oxalate) | 65 | 206–8 |
| 20 | 3 | NH$_2$ | 1-piperidinyl | 91 | 142–4 |
| 21 | 3 | CN | 1-piperidinyl | 27 | 208–10 |
| 22 | 3 | I | 1-piperidinyl | 55 | 176–8 |
| 23 | 3 | I | 1-piperidinyl | 25 | 80–2 |

TABLE 1-continued

Prepared products 1 - 21: Hydrochlorides acc. to formula (I)

| No. | n. | Y | NR¹R² | Yield (%) | melting point (°C) |
|-----|----|----|-------|-----------|-------------------|
| 24 | 4 | NO$_2$ | 1-piperidinyl | 92 | 100–3 |
| 25 | 4 | NH$_2$ | 1-piperidinyl | 85 | 216–8 |
| 26 | 2 | Br | 1-piperidinyl | 64 | 174–5 |
| 27 | 3 | Br | 1-piperidinyl | 33 | 154–6 |
| 28 | 4 | Br | 1-piperidinyl | 32 | 155–7 |
| 29 | 2 | NO$_2$ | 1-homopiperidinyl | 71 | 169–70 |

Examples for synthesis method B: Preparation of N-[2-(1-piperidinyl)ethyl]-4-amino-2-phenoxymethane sulfanilide-hydrochloride (9)

A hydrogenation flask was filled with 4.56 g N-[2-(1-piperidinyl)ethyl]-4-nitro-2-phenoxymethane sulfanilide-hydrochloride (3) together with 0.5 g Pd (5% in C) and 300 ml 0.2 HCl. The reaction was performed in an H$_2$-atmosphere with 50 psi and under stirring for about 3 h at ambient temperature. Thereafter it was filtered through a celite bed and the solvent of the filtrate was evaporated and a yield of 90% of the title product was obtained. After recrystallization in absolute ethanol, the melting point was determined to be 220°–2° C.

Analogously therewith and starting from N-[2-(diethylamino)ethyl]-4-nitro-2-phenoxymethane sulfanilidine-hydrochloride (2), a yield of 80% of N-(2-(diethylamino)ethyl)-4-amino-2-phenoxymethane sulfanilidine-hydrochloride (10) having a melting point of 160°–2° C. was obtained.

Analogously therewith and starting from N-[3-(1-piperidinyl)propyl]-4-nitro-2-phenoxymethane sulfanilide-hydrochloride (8), a yield of 91% of N-[2-(1-piperidinyl)propyl]-4-amino-2phenoxymethane sulfanilide-hydrochloride (20) having a melting point of 142-4 was obtained.

Examples for synthesis method C: Preparation of N-[2-(diethylamino)ethyl]-4-acetamide-2-phenoxymethane sulfanilide-hydrochloride (11)

A solution of 1.8 g N-[2-(diethylamino)ethyl]-4-amino-2-phenoxymethane sulfanilide-hydrochloride (10) was reacted in 20 ml water with 0.6 g acetic acid anhydride at 25° C. for 3 h. The reaction mixture was made alkaline with sodium hydroxide and extracted with dichloromethane. The organic extract was washed in water several times and dried with sodium sulfate, and the solvent was evaporated. The residue was dissolved in absolute ethanol and a solution of HCl (10% in ethanole) was added whereby a yield of 87% of title product (1) was obtained. After recristallization the melting point was determined to be 183°–5° C.

Analogously therewith and starting from N-[2-(1-piperidinyl)ethyl]-4-amino-2-phenoxymethane sulfanilide-hydrochloride (9) a yield of 98% of N-[2-(1-piperidinyl)ethyl]-4-acetamido-2-phenoxymethane sulfanilide-hydrochloride (12) was obtained having a melting point of 158°–9° C.

Examples for synthesis method D (Sandmeyer reaction): Preparation of N-[2-(1-piperidinyl)ethyl]-4-cyano-2-phenoxymethane sulfanilide-oxalate (19)

A solution of 0.42 g sodium nitrite in 10 ml water was dropped into a mixture of 0.42 g N-[2-(1-piperidinyl)ethyl]-4-amino-2-phenoxymethane sulfanilide-hydrochloride (9), 1 ml HCl (conc.) and 5 ml water at 0°–5° C. and all that was stirred for 20 min. after the addition. The mixture was neutralized with NaHCO$_3$ and a solution of 2.6 g potassium cyanide and 1 g copper chloride in 10 ml water was slowly added at 5°–10° C. The mixture kept at ambient temperature for 30 min. and then heated to 50° C. for 30 min. The reaction mixture, cooled down to ambient temperature, was extracted with ethyl acetate. The organic phase was washed with water, dried, and the solvent was evaporated. The residue was dissolved in 10 ml ethanol and 0.6 g anhydrous oxalic acid was added to the solution. The mixture was kept at ambient temperature for about 1 h and thereafter in an ice bath for 2 h. The mixture was filtered and washed in cold ethanol, a yield of 65% of the title product (19) having been obtained. After recristallization the melting point was determined to be 205°–8° C.

Analogously therewith and starting from N-[3-(1-piperidinyl)propyl]-4-amino-2-phenoxymethane sulfanilide-hydrochloride (20), upon addition of HCl instead of oxalic acid, a yield of 27% of N-[3-(1-piperidinyl)propyl]-4-cyano-2-phenoxymethane sulfanilide-hydrochloride (21) having a melting point of 208°–10° C. was obtained. Starting from amino (20), where the copper cyanide was substituted by copper jodide, however, a product (23) was obtained; and starting from amino (9), a product (22) with the yield and the melting points as indicated in the table was obtained.

Examples of application: Experiments as regards the antispasmodic action

Experiments as regards the antispasmodic action were performed with each of the products of table 2, one in comparison with acetylcholine (Ac-Col) and another one with BaCl$_2$ (cf. G. Toson et al., *Arzneim. Forsch.* 1978, Volume 28, (II), page 1130).

The experiment concerning the inhibiting action with the acetylcholine (Ac-Col) induced contraction was performed at the Ileus of a male Winstar-rat having a weight of 200–300 g in a 10 ml bath with a tyrode solution at 37° C., gas-purged with 95% O$_2$ and 5% N$_2$ and one gram potential. The contraction reaction was measured with an isotonic converter. The contraction was induced with acetylcholine at increasing dosages of $10^{-9}$ to $10^{-2}$ M. The experimental products were administered 5 min. before acetylcholine. Three or more dosage levels were used and the DE$_{50}$ were measured and indicated in mol concentration (M).

The experiment concerning the inhibitory action with the contraction induced by BaCl$_2$ was made under analogous conditions, but the contraction was triggered with increasing dosages from $5\times10^{-5}$ to $10^{-3}$ M.

TABLE 2

Antispasmodic action of some products in vitro

| No. | DE50 ($10^{-6}$ M) vs. Ac-Col. | DE50 ($10^{-6}$ M) vs BaCl$_2$ |
|-----|-------------------------------|-------------------------------|
| 1 | 4.99 | 6.45 |
| 2 | 12.4 | 9.37 |
| 3 | 9.38 | 3.65 |
| 4 | 18.4 | 7.31 |
| 5 | 4.89 | 5.06 |
| 6 | 2.5 | 134 |
| 8 | 9.08 | 8.64 |
| 15 | 13.9 | 11.5 |
| 16 | 26.9 | 10.9 |
| 17 | 11.2 | 7.37 |
| 19 | 9.22 | 9.79 |
| 21 | 8.94 | 14.4 |
| 23 | 0.90 | 1.04 |
| 26 | 1.00 | 0.94 |
| 27 | 1.30 | 1.90 |
| 28 | 5.65 | 4.78 |
| 29 | 1.58 | 1.61 |

We claim:

1. A method of treating an animal or patient in which alleviation of smooth muscle spasm is indicated, wherein an amount of the compound according to formula (I) effective to treat smooth muscle spasm is administered to an animal or patient in which such treatment is indicated,

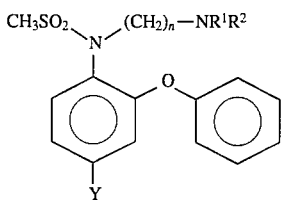

wherein

Y represents hydrogen, cyano, nitro, amino, acetamide or halogen;

n is an integer between 2 and 4;

$R^1$ and $R^2$, which are equal or different are (C1-C4)-alkyl or are connected with each other and via the N-atom, thereby forming a 1-pyrrolidinyl, 1-piperidinyl, 1-piperazinyl, 4-methyl-1-piperazinyl, 4-ethylpiperazinyl, 4-propylpiperazinyl, 1-homopiperidinyl or 4-morpholine residue.

2. The method according to claim 1 wherein said administered compound is in solution.

3. The method according to claim 1 wherein said compound further comprises a pharmaceutically acceptable addition salt.

4. The method according to claim 1 wherein said amount of said compound is administered in unit dosage form.

* * * * *